US00PP28374P3

(12) United States Plant Patent
Klemm et al.

(10) Patent No.: US PP28,374 P3
(45) Date of Patent: Sep. 12, 2017

(54) ***CALCEOLARIA* PLANT NAMED 'KLECH15023'**

(50) Latin Name: ***Caleceolaria* hybrid**
Varietal Denomination: KLECH15023

(71) Applicant: Klemm+Sohn GmbH & Co. KG, Stuttgart (DE)

(72) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 96 days.

(21) Appl. No.: 14/998,561

(22) Filed: Jan. 19, 2016

(65) Prior Publication Data

US 2017/0208722 P1 Jul. 20, 2017

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — Barbara Campbell; Bethany R. Roahrig; Cochran Freund & Young, LLC

(57) ABSTRACT

A new *calceolaria* plant particularly distinguished by having red flowers, and medium-late earliness to flower, is disclosed.

1 Drawing Sheet

Genus and species: *Calceolaria* hybrid.
Variety denomination: 'KLECH15023'.

BACKGROUND OF THE NEW PLANT

The present invention comprises a new and distinct variety of *calceolaria*, botanically known as *Calceolaria* hybrid and hereinafter referred to by the variety name 'KLECH15023'. 'KLECH15023' was derived as a selection from the hand-crossing between the proprietary *calceolaria* female parent 'CH-2006-0095' (unpatented) and the proprietary male *calceolaria* parent 'CH-2007-0027' (unpatented) in June 2008 in Stuttgart, Germany.

Seeds from the initial hand-crossing were planted in Stuttgart, Germany and a single plant was selected in May 2009 and subsequently named 'KLECH15023'.

In June 2009, 'KLECH15023' was first asexually propagated by vegetative stem cuttings. 'KLECH15023' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Red flowers; and
2. Medium-late earliness to flower.

CROSS-REFERENCE TO RELATED APPLICATIONS

An application with the Canadian Plant Breeders Rights Office was filed for this variety on Apr. 2, 2015, Application No. 15/8564.

DESCRIPTION OF THE PHOTOGRAPH

This new *calceolaria* plant is illustrated by the accompanying photograph which shows an overall view of the whole plant. The photograph is of a plant approximately eleven-weeks-old grown in a greenhouse in Stuttgart, Germany in April 2012.

The colors shown are as true as can be reasonably obtained by conventional photographic procedures.

DESCRIPTION OF THE NEW VARIETY

The following detailed descriptions set forth the distinctive characteristics of 'KLECH15023'. The data which define these characteristics were collected from asexual reproductions carried out in Stuttgart, Germany. Data was collected on ten-week-old plants grown indoors in Stuttgart, Germany under greenhouse conditions in November 2015. Color references are to The R.H.S. Colour Chart of The Royal Horticultural Society of London (R.H.S.), 5$^{th}$ edition (2007).

Classification:

*Family*.—Scrophulariaceae or Calceolarieaceae.

*Common name*.—Lady's purse, slipper flower, pocketbook flower.

Parentage:

*Female parent*.—The proprietary *calceolaria* female parent 'CH-2006-0095' (unpatented).

*Male parent*.—The proprietary male *calceolaria* parent 'CH-2007-0027' (unpatented).

Plant description:

*Type*.—Potted plant.

*Habit*.—Upright.

*Plant height*.—Approximately 20.0 cm.

*Plant width*.—Approximately 16.0 cm.

*Flowering habit*.—Continuous, but intermittent in the summer.

*Time to produce a finished flowering plant*.—Approximately 12 weeks for a 12 cm pot.

*Propagation type*.—Cuttings.

*Time to initiate roots*.—5 to 6 weeks.

*Root description*.—Adventitious, fibrous root system, with fine light brown, RHS 164C roots.

Stems:

*Quantity per plant*.—4 to 6.

*Color*.—RHS 187B base at the base; tip is RHS 145B.

*Length*.—Approximately 5.0 cm.

*Diameter*.—Approximately 0.5 cm.

*Internode length*.—Approximately 1.5 cm.

*Texture*.—Very small and soft hairs, less pubescent.

*Anthocyanin*.—Present, stems dark red at the base, RHS 187B, and light green, RHS 145B at the tip.

Leaves:

*Arrangement*.—Decussate.

*Length*.—Mature leaves are 9.0 cm.

*Width*.—Mature leaves are 5.0 cm.

*Shape*.—Rhombical.

*Apex*.—Obtuse.

*Base*.—Attenuate.

*Margin*.—Crenate.

*Texture* (*both surfaces*).—Leathery, smooth.

*Glossiness of the leaf blade*.—Weak.

*Color*.—Immature leaf: Upper surface: RHS 137B. Lower surface: RHS 146B. Mature leaf: Upper surface: RHS 137A. Lower surface: RHS 147B.

*Venation pattern*.—Reticulate.

*Venation color*.—Upper surface: RHS 148C. Lower surface: RHS 144D.

*Petiole*.—Length: Approximately 2.5 cm. Diameter: 0.7 cm to 1.0 cm. Color: RHS 145B with RHS 185C anthocyanin. Texture: Pubescent, with fine hairs.

Flowers:

*General*.—Zygomorphic with a four-parted calyx, with the lobes free to the base, and a two-lipped sympetalous corolla.

*Flowering season*.—From May to June and August to October, without artificial light.

*Lastingness of individual flowers on the plant*.—About 14 days.

*Fragrance*.—Absent.

*Flower length*.—Approximately 3.5 cm.

*Flower width*.—Approximately 3.0 cm.

*Bud*.—Shape: Truncate hemisphere. Height: Approximately 0.3 cm. Width: Approximately 0.6 cm. Color: RHS 144A. Texture: Velvety.

*Corolla*.—General: The corolla is two-lipped and composed of two pouches, the upper lip and the lower lip. Upper lip: Hood: Present, RHS 46, with light yellow border of RHS 13A. Length: Approximately 0.6 cm. Width: Approximately 0.3 cm. Texture: Upper surface: Velvety. Lower surface: Smooth. Color: Immature: RHS N34A and RHS 1B. Mature: RHS 46A and RHS 13A. Shape: Hemispherical. Apex: Elliptic. Base: Fused with the lower lip. Margin: Entire. Lower lip: Length: 1.5 cm. Width: 2.0 cm. Texture: Upper surface: Velvety. Lower surface: Smooth. Color: Immature: RHS N34A. Mature: RHS 46A. Shape: Hemispherical. Apex: Elliptic. Base: Fused with upper lip. Margin: Entire. Oil gland: Absent.

*Calyx*.—Four-parted calyx, all calyx lobes with similar size. Sepals: Upper sepal: Length: Approximately 0.7 cm. Width: Approximately 0.5 cm. Color: Upper surface: RHS 137C. Lower surface: RHS 137B. Texture: Pubescent, small fine hairs. Shape: Ovate with acuminate sepal tip. Apex: Acuminate. Base: Fused with other sepals. Margin: Entire. Lateral sepals: Length: Approximately 0.7 cm. Width: Approximately 0.5 cm. Color: Upper surface: RHS 137C. Lower surface: RHS 137B. Texture: Pubescent with small fine hairs. Shape: Ovate with acuminate sepal tip. Apex: Acuminate. Base: Fused with other sepals. Margin: Entire.

*Pedicel*.—Length: Approximately 2.0 cm. Diameter: Approximately 0.1 cm. Color: RHS N199A. Texture: Smooth.

*Peduncle*.—Length: Approximately 7.0 cm. Diameter: Approximately 0.3 cm. Color: RHS 152B. Texture: Pubescent, sticky.

Reproductive organs:

*Stamens*.—Quantity per flower: 2. Anther shape: Elliptic. Anther length: 0.1 cm. Anther diameter: Approximately 0.1 mm. Anther color: RHS 11B. Filament length: Approximately 0.2 cm. Pollen amount: Scarce. Pollen color: RHS 11B.

*Pistils*.—Quantity per flower: 1. Pistil length: 0.5 cm. Style length: 0.4 cm. Style color: RHS 53A. Stigma shape: Tube-like. Stigma color: RHS 13A. Ovary color: RHS 53A. Ovary shape: Cylindrical.

Fruit and seed set: After pollination, capsulates are developed. The capsulates are ovate-shaped, seeds are dark brown, RHS 200A, seeds are ovate and less than 0.1 cm in size.

Disease and insect resistance: No particular disease or insect resistance observed.

COMPARISON WITH PARENTAL LINES AND KNOWN VARIETY

'KLECH15023' is distinguished from its parental lines as described in Table 1.

TABLE 1

| Characteristic | 'KLECH15023' | Female parent 'CH-2006-0095' | Male parent 'CH-2007-0027' |
|---|---|---|---|
| Vigor | Low | High | Medium |
| Flower color | Red | Orange-red | Orange-red |

'KLECH15023' can be compared to the commercial *calceolaria* plant variety 'KLECH13020' (U.S. Publication No. 2015-0319903). Differences between the two varieties are described in Table 2.

TABLE 2

| Comparison with Similar Variety | | |
|---|---|---|
| Characteristic | 'KLECH15023' | 'KLECH13020' |
| Flower color | Red | Dark red |
| Plant habit | Small/tiny | Medium |
| Earliness to flower | Medium-late | Early |

We claim:

1. A new and distinct variety of *calceolaria* plant named 'KLECH15023' as illustrated and described herein.

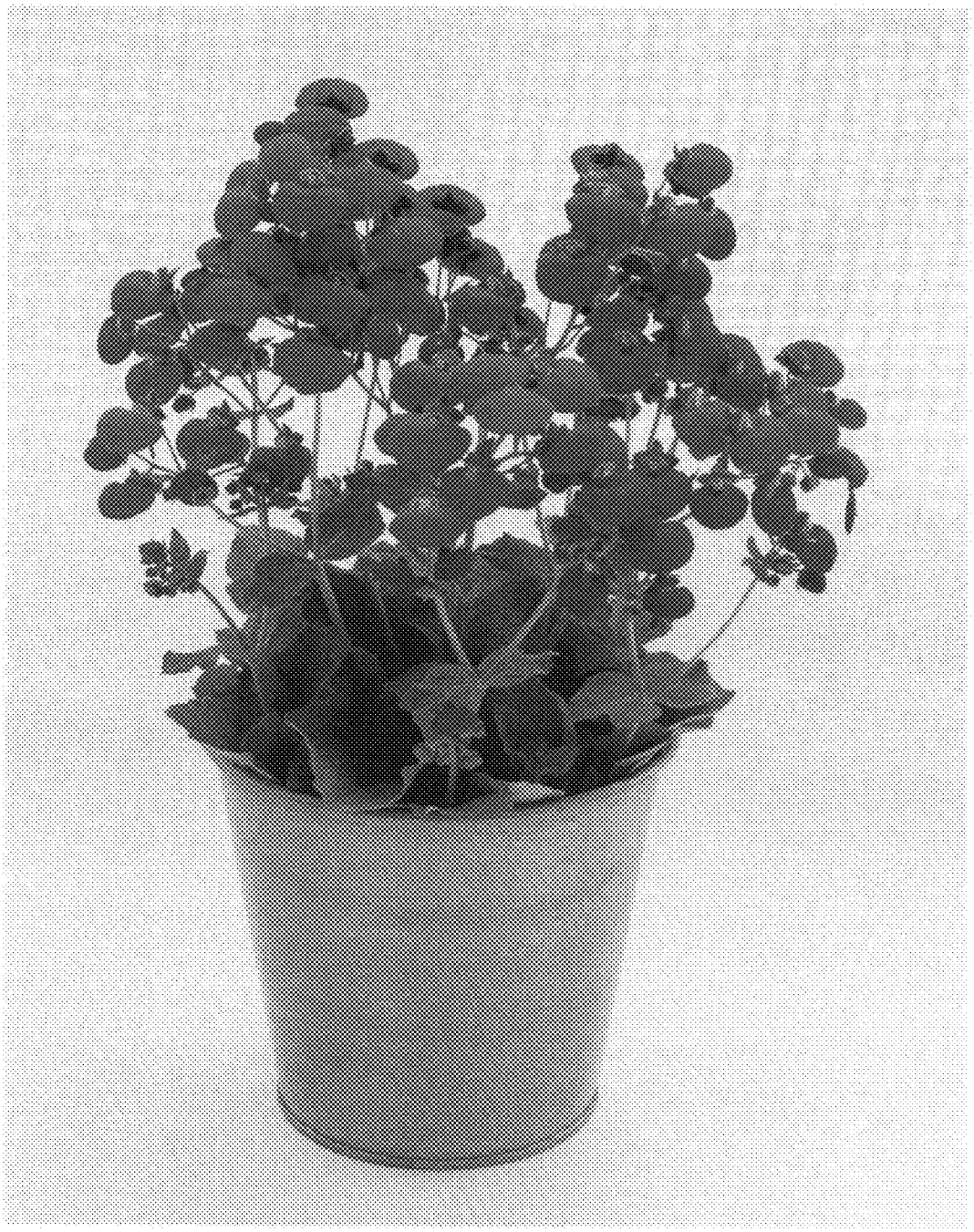

* * * * *